(12) United States Patent
Hirose

(10) Patent No.: US 10,688,655 B2
(45) Date of Patent: Jun. 23, 2020

(54) MEDICAL OBSERVATION APPARATUS, MEDICAL OBSERVATION SYSTEM, AND CONTROL METHOD

(71) Applicant: Sony Olympus Medical Solutions Inc., Tokyo (JP)

(72) Inventor: Kenji Hirose, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 129 days.

(21) Appl. No.: 15/705,823

(22) Filed: Sep. 15, 2017

(65) Prior Publication Data

US 2018/0085915 A1    Mar. 29, 2018

(30) Foreign Application Priority Data

Sep. 23, 2016 (JP) .................. 2016-186263

(51) Int. Cl.

| A61B 90/20 | (2016.01) |
|---|---|
| B25J 9/04 | (2006.01) |
| B25J 17/00 | (2006.01) |
| B25J 9/12 | (2006.01) |
| F16D 7/02 | (2006.01) |
| A61B 90/25 | (2016.01) |
| A61B 90/00 | (2016.01) |
| H02P 5/00 | (2016.01) |
| G05B 1/00 | (2006.01) |

(Continued)

(52) U.S. Cl.
CPC .............. *B25J 9/04* (2013.01); *A61B 90/25* (2016.02); *A61B 90/37* (2016.02); *B25J 9/126* (2013.01); *B25J 17/00* (2013.01); *F16D 7/02* (2013.01); *F16D 27/112* (2013.01); *G05B 1/00* (2013.01); *H02P 5/00* (2013.01); *H02P 5/74* (2013.01); *A61B 2090/373* (2016.02); *Y10S 901/02* (2013.01); *Y10S 901/15* (2013.01); *Y10S 901/23* (2013.01); *Y10S 901/44* (2013.01)

(58) Field of Classification Search
CPC .... B25J 17/00; B25J 9/04; B25J 9/126; F16D 7/02; H02P 5/00; H02P 5/74; Y10S 901/02; Y10S 901/15; Y10S 901/23
USPC ................................ 700/245; 600/101–104
See application file for complete search history.

(56) References Cited

U.S. PATENT DOCUMENTS

| 8,038,108 | B2 * | 10/2011 | Yasunaga | A61B 90/25 248/123.2 |
|---|---|---|---|---|
| 2004/0138524 | A1 * | 7/2004 | Ueda | A61B 90/50 600/102 |
| 2012/0296159 | A1 * | 11/2012 | Kanazawa | A61B 1/00128 600/102 |

FOREIGN PATENT DOCUMENTS

JP         11-244301        9/1999

* cited by examiner

*Primary Examiner* — Dalena Tran
(74) *Attorney, Agent, or Firm* — Xsensus LLP

(57) ABSTRACT

A medical observation apparatus includes: an imaging unit; a support unit including arms, a first joint that connects two of the arms and relatively rotates the two arms about a first rotation axis in accordance with given power, a second joint that connects two of the arms and relatively rotates the two arms about a second rotation axis in accordance with given power, a first motor that gives the power to the first joint, and a second motor that gives the power to the second joint; and a controller configured to control a rotational speed of the first motor in accordance with a first speed profile until the rotational speed reaches a predetermined operational speed, and control, until the rotational speed reaches the predetermined operational speed, a rotational speed of the second (Continued)

motor in accordance with a second speed profile that is different from the first speed profile.

17 Claims, 9 Drawing Sheets

(51) Int. Cl.
*H02P 5/74* (2006.01)
*F16D 27/112* (2006.01)

| WD (mm) | OPTICAL ZOOM | | ELECTRONIC ZOOM OFF |
|---|---|---|---|
| 200.00 | WIDE | 1x | 90.0 |
| | TELE | 6x | 15.0 |
| 400.00 | WIDE | 1x | 150.0 |
| | TELE | 6x | 25.0 |
| 600.00 | WIDE | 1x | 210.0 |
| | TELE | 6x | 35.0 |

| MOVING DIRECTION | X-AXIAL MOTOR | Y-AXIAL MOTOR |
|---|---|---|
| Ar1 | - | CW |
| Ar2 | CCW | CW |
| Ar3 | CCW | - |
| Ar4 | CCW | CCW |
| Ar5 | - | CCW |
| Ar6 | CW | CCW |
| Ar7 | CW | - |
| Ar8 | CW | CW |

MEDICAL OBSERVATION APPARATUS, MEDICAL OBSERVATION SYSTEM, AND CONTROL METHOD

CROSS-REFERENCE TO RELATED APPLICATION

The present application claims priority to and incorporates by reference the entire contents of Japanese Patent Application No. 2016-186263 filed in Japan on Sep. 23, 2016.

BACKGROUND

The present disclosure relates to a medical observation apparatus, a medical observation system, and a control method.

In the related art, known is a medical observation apparatus including a magnifying optical system for observing a microscopic site of a part under operation of a patient in a magnified manner and a support unit that has a plurality of arms and a plurality of joints that connect the arms with each other and supports the magnifying optical system at the distal end thereof (refer to Japanese Laid-open Patent Publication No. 11-244301, for example).

In the medical observation apparatus described in Japanese Laid-open Patent Publication No. 11-244301, the joints include the following X- and Y-axial joints described below.

The X-axial joint connects two arms of the arms with each other, rotates the two arms relatively about an X-axis orthogonal to an observation optical axis of the magnifying optical system in accordance with given power, and moves a field of view by the magnifying optical system along the observation optical axis and a Y-axis orthogonal to the X-axis.

The Y-axial joint connects two arms of the arms with each other, rotates the two arms relatively about the Y-axis in accordance with given power, and moves the field of view by the magnifying optical system along the X-axis.

The medical observation apparatus described in Japanese Laid-open Patent Publication No. 11-244301 includes an X-axial motor that gives power to the X-axial joint, a Y-axial motor that gives power to the Y-axial joint, an operation receiving unit that receives a user operation, and a controller that controls each operation of the X-axial motor and the Y-axial motor in accordance with the user operation.

SUMMARY

In recent years, in the medical observation apparatus, proposed is a configuration in which an imaging unit that images a target object in a magnified manner is provided in place of the magnifying optical system and an external display apparatus is caused to display an image taken by the imaging unit. The medical observation apparatus that thus uses the imaging unit and moves the imaging unit in a three-dimensional manner using the motion of the joints has the following problem.

Specifically, the problem is that observation with a higher magnification gives a narrower imaging field of view by the imaging unit, and when a weak force is applied to the imaging unit alone (when the imaging unit is slightly moved alone), a target site in the target object disappears from the screen of the display apparatus (an image vanishes).

The provision of the following X- and Y-axial load imparting mechanisms is considered in order to prevent such image vanishing.

The X-axial load imparting mechanism is a mechanism that, when two arms connected with an X-axial joint relatively rotate, imparts rotational resistance caused by friction to the rotation.

The Y-axial load imparting mechanism is a mechanism that, when two arms connected with a Y-axial joint relatively rotate, imparts rotational resistance caused by friction to the rotation.

The provision of the X- and Y-axial load imparting mechanisms described above gives a structure in which it is difficult to move the imaging unit by the application of a weak force to the imaging unit alone and may prevent image vanishing when the target object is being observed with a high magnification.

The X-axial joint is provided on the distal end side of the support unit relative to the Y-axial joint. For this reason, the Y-axial joint is heavier in the weight of an object to be rotated and is larger in inertial force than the X-axial joint. The separate distance between an X-axis and a gripped position (a position that an operator holds (the imaging unit, for example)) and the separate distance between a Y-axis and the gripped position are different from each other, and the easiness of rotation about the X-axis by the X-axial joint and the easiness of rotation about the Y-axis by the Y-axial joint are different from each other. For this reason, considering the point described above, the respective frictional forces of the rotational resistance that the X- and Y-axial load imparting mechanisms impart are made different from each other.

When the respective frictional forces of the rotational resistance that the X- and Y-axial load imparting mechanisms impart are made different from each other, the following problem arises, for example.

The following assumes that the Y-axial load imparting mechanism is set to be stronger than the X-axial load imparting mechanism in the frictional force of the rotational resistance to be imparted for the convenience of description.

First, assumed is a case in which the X-axial motor starts to be driven, and until the rotational speed of the X-axial motor reaches a first operational speed, the rotational speed is controlled in accordance with a first speed profile.

In this case, the two arms connected with the X-axial joint do not relatively rotate simultaneously when the X-axial motor starts to be driven and start to rotate after a first time has elapsed after the X-axial motor has started to be driven. This is ascribable to the fact that an X-axial power transmission mechanism such as gears that transmits the rotation of the X-axial motor to the X-axial joint gradually becomes elastically deformed in accordance with the rotation of the X-axial motor until balancing with the frictional force of the rotational resistance by the X-axial load imparting mechanism. In other words, at a point in time when the amount of elastic deformation of the X-axial load imparting mechanism has exceeded a predetermined amount responsive to the frictional force (after the first time has elapsed), the two arms connected with the X-axial joint start to relatively rotate.

Next, assumed is a case in which the Y-axial motor starts to be driven, and until the rotational speed of the Y-axial motor reaches the first operational speed, the rotational speed is controlled in accordance with the first speed profile similarly to the case of the X-axial motor.

In this case, the two arms connected with the Y-axial joint do not relatively rotate simultaneously when the Y-axial motor starts to be driven and start to rotate after a second time, which is later than the time after the first time has elapsed, has elapsed after the Y-axial motor has started to be driven. This is ascribable to the fact that a Y-axial power transmission mechanism such as gears that transmits the rotation of the Y-axial motor to the Y-axial joint gradually becomes elastically deformed in accordance with the rotation of the Y-axial motor until balancing with the frictional force of the rotational resistance by the Y-axial load imparting mechanism (a frictional force stronger than the frictional force of the rotational resistance by the X-axial load imparting mechanism). In other words, when the amount of elastic deformation of the Y-axial load imparting mechanism has exceeded a predetermined amount responsive to the frictional force (after the second time has elapsed), the two arms connected with the Y-axial joint start to relatively rotate.

As described above, when the rotational speeds of the X- and Y-axial motors are controlled in accordance with the same speed profile, the relative rotation of the two arms the imparted frictional force of which is weaker (connected with the X-axial joint) starts first. After that, the relative rotation of the two arms the imparted frictional force of which is stronger (connected with the Y-axial joint) starts. For this reason, when a user operation to move the imaging field of view in an oblique direction crossing the X-axis and the Y-axis is performed on the operation receiving unit (when both the X- and Y-axial motors are operated), the imaging field of view will first move in the Y-axial direction, and the imaging field of view will then move in the oblique direction. Consequently, a problem arises in that the operator who checks the image displayed on the display apparatus is given an uncomfortable feeling.

A medical observation apparatus according to one aspect of the present disclosure includes: an imaging unit configured to image a target object in a magnified manner; a support unit configured to support the imaging unit, the support unit including a plurality of arms, a first joint that connects two of the arms with each other and relatively rotates the two arms about a first rotation axis in accordance with given power, a second joint that connects two of the arms with each other and relatively rotates the two arms about a second rotation axis in accordance with given power, a first motor that gives the power to the first joint, and a second motor that gives the power to the second joint; and a controller configured to control a rotational speed of the first motor in accordance with a first speed profile until the rotational speed reaches a predetermined operational speed, and control, until the rotational speed reaches the predetermined operational speed, a rotational speed of the second motor in accordance with a second speed profile that is different from the first speed profile.

A medical observation apparatus according to another aspect of the present disclosure includes: an imaging unit configured to image a target object in a magnified manner; a support unit configured to support the imaging unit, the support unit including a plurality of arms, a first joint that connects two of the arms with each other and relatively rotates the two arms about a first rotation axis in accordance with given power, a second joint that connects two of the arms with each other and relatively rotates the two arms about a second rotation axis in accordance with given power, a first motor that gives power to the first joint, and a second motor that gives power to the second joint; and a controller configured to simultaneously start relative rotation of the two arms connected with the first joint and relative rotation of the two arms connected with the second joint.

DETAILED DESCRIPTION

Figure 1:
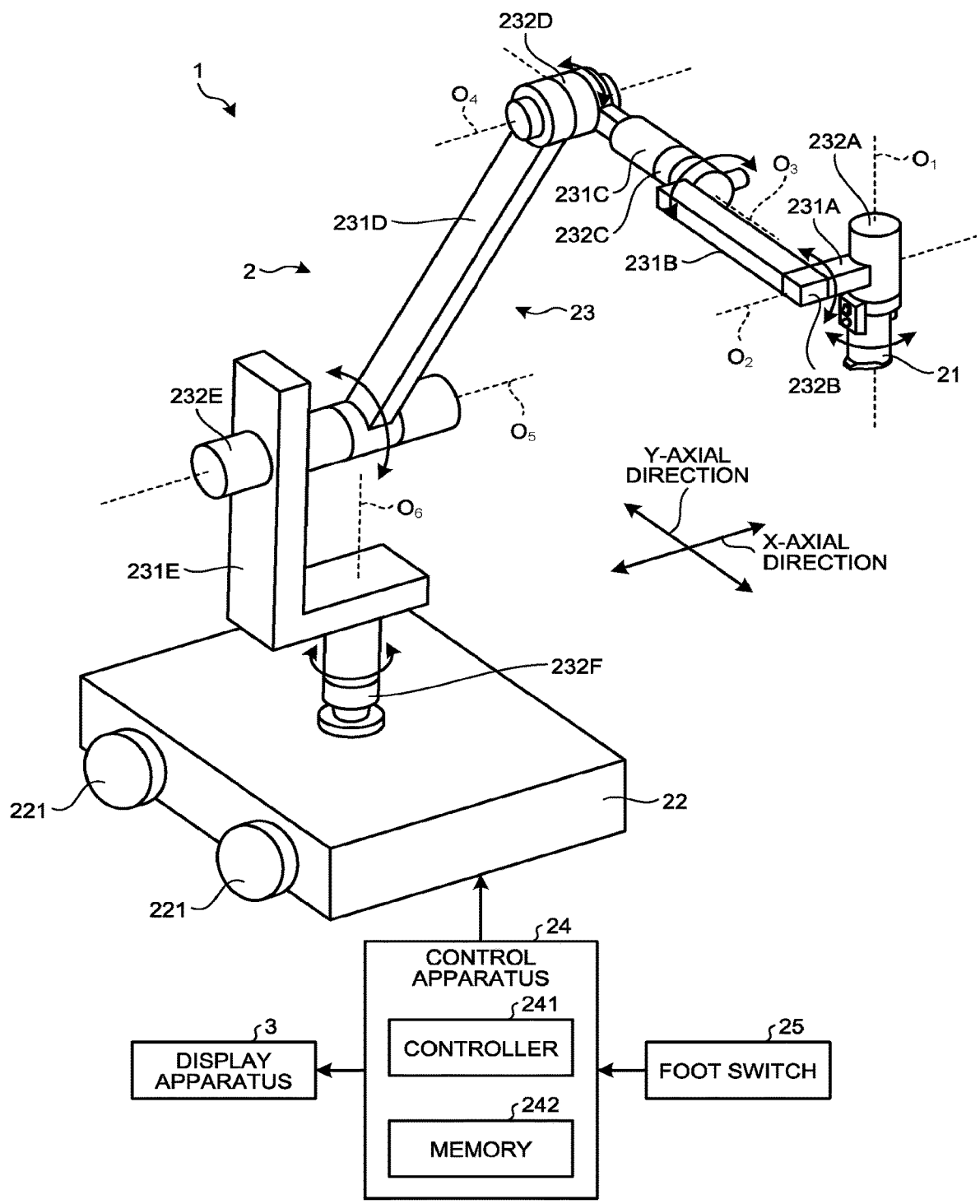
FIG. 1 is a diagram of a schematic configuration of a medical observation system according to a first embodiment.

The following describes embodiments for performing the present disclosure (hereinafter, embodiments) with reference to the accompanying drawings. The embodiments described below do not limit the present disclosure. Further, in the drawings, the same components are denoted by the same symbols.

Schematic Configuration of Medical Observation System

FIG. 1 is a diagram of a schematic configuration of a medical observation system 1 according to a first embodiment.

The medical observation system 1 is a system that images a site (a target object) as an object to be treated by an operator during an operation or an examination in a magnified manner and displays an image responsive to the imaging. As illustrated in FIG. 1, this medical observation system 1 includes a medical observation apparatus 2 that images the target object and outputs an image signal and a display apparatus 3 that displays an image based on the image signal output from the medical observation apparatus 2.

As illustrated in FIG. 1, the medical observation apparatus 2 includes an imaging unit 21, a base 22, a support unit 23, a control apparatus 24, and a foot switch 25.

The imaging unit 21 images the target object in a magnified manner and outputs the image signal responsive to the imaging. This imaging unit 21 includes any of various kinds of known optical systems and any of various kinds of known imaging elements such as a charge coupled device (CCD) sensor and a complementary metal-oxide-semiconductor (CMOS) sensor that receives light collected by the optical system and converts the light into an electric signal, for example. This imaging unit 21 also installs various kinds of functions such as an auto focus (AF) function and an optical zooming function. The imaging unit 21 may be configured as what is called a stereo camera including a pair of imaging elements.

The base 22 is a base of the medical observation apparatus 2 and is movable on the surface of a floor via casters 221 (FIG. 1).

The support unit 23 extends from the base 22 and holds the imaging unit 21 at the distal end thereof (an end separate from the base 22). The support unit 23 enables the imaging unit 21 to move in a three-dimensional manner in accordance with an operation by the operator.

Although the support unit 23 has six degrees of freedom for the movement of the imaging unit 21 in the first embodiment, this is not limiting; the number of degrees of freedom thereof may be any other number.

As illustrated in FIG. 1, this support unit 23 includes first to fifth arms 231A to 231E and first to sixth joints 232A to 232F.

A detailed configuration of the first to sixth joints 232A to 232F will be described below with the second and third joints 232B and 232C as examples; they each have a fixed part and movable part and have a structure in which the movable part is rotatable relative to the fixed part.

The first joint 232A is positioned at the distal end of the support unit 23 and has a cylindrical shape. This first joint 232A holds the imaging unit 21 with the movable part (not illustrated) positioned inside the cylinder and is supported by the first arm 231A with the fixed part (not illustrated) positioned outside the cylinder. In the first joint 232A, the movable part is rotatable about a first axis $O_1$ relative to the fixed part. Consequently, the first joint 232A enables the imaging unit 21 to rotate about the first axis $O_1$.

The first axis $O_1$ is a central axis of the cylinder of the first joint 232A and is an axis overlapping with an observation optical axis of the imaging unit 21 held by the first joint 232A.

In other words, when the imaging unit 21 is rotated about the first axis $O_1$, the orientation of an imaging field of view by the imaging unit 21 is changed.

The first arm 231A extends from a side face of the first joint 232A in a direction orthogonal to the first axis $O_1$ and supports the first joint 232A (the fixed part) at the distal end thereof.

The second joint 232B is connected to the basal end of the first arm 231A with a movable part 233 (refer to FIG. 5) positioned on the distal end side and is connected to the second arm 231B with a fixed part 234 (refer to FIG. 5) positioned on the basal end side (a side close to the base 22). In the second joint 232B, the movable part 233 is rotatable about a second axis $O_2$ relative to the fixed part 234. Consequently, the second joint 232B enables the first arm 231A (the imaging unit 21) to rotate about the second axis $O_2$.

The second axis $O_2$ is an axis orthogonal to the first axis $O_1$ and parallel to the extension direction of the first arm 231A and corresponds to a first rotation axis according to the present disclosure (the X-axis illustrated in FIG. 1).

In other words, when the imaging unit 21 is rotated about the second axis $O_2$, the orientation of the optical axis of the imaging unit 21 relative to the target object is changed. In still other words, the imaging field of view by the imaging unit 21 moves along the Y-axis (FIG. 1) orthogonal to the first and second axes $O_1$ and $O_2$. Consequently, the second joint 232B is a joint that causes the imaging field of view by the imaging unit 21 to move along the Y-axis. The second joint 232B corresponds to a first joint according to the present disclosure.

The second arm 231B has a crank shape extending in a direction orthogonal to the first and second axes $O_1$ and $O_2$ and supports the second joint 232B (the fixed part 234) at the distal end thereof.

The third joint 232C is connected to the basal end of the second arm 231B with a movable part 235 (refer to FIG. 5) positioned on the distal end side and is connected to the third arm 231C with a fixed part 236 (refer to FIG. 5) positioned on the basal end side. In the third joint 232C, the movable part 235 is rotatable about a third axis $O_3$ relative to the fixed part 236. Consequently, the third joint 232C enables the second arm 231B (the imaging unit 21) to rotate about the third axis $O_3$.

The third axis $O_3$ is an axis orthogonal to the first and second axes $O_1$ and $O_2$ and corresponds to a second rotation axis according to the present disclosure (the Y-axis).

In other words, when the imaging unit 21 is rotated about the third axis $O_3$, the orientation of the optical axis of the imaging unit 21 relative to the target object is changed. In still other words, the imaging field of view by the imaging unit 21 moves along the X-axis (FIG. 1). Consequently, the third joint 232C is a joint that causes the imaging field of view by the imaging unit 21 to move along the X-axis. The third joint 232C corresponds to a second joint according to the present disclosure.

The third arm 231C extends in a direction substantially parallel to the extension direction of the second arm 231B and supports the third joint 232C (the fixed part 236) at the distal end thereof.

The fourth joint 232D extends substantially parallel to the second axis $O_2$, is connected to the basal end of the third arm 231C with the movable part (not illustrated) positioned on one end side, and is connected to the fourth arm 231D with the fixed part (not illustrated) positioned on the other end side. In the fourth joint 232D, the movable part is rotatable about a fourth axis $O_4$ relative to the fixed part. Consequently, the fourth joint 232D enables the third arm 231C (the imaging unit 21) to rotate about the fourth axis $O_4$.

The fourth axis $O_4$ is an axis orthogonal to the third axis $O_3$.

In other words, when the imaging unit 21 is rotated about the fourth axis $O_4$, the height of the imaging unit 21 relative to the target object is adjusted.

The fourth arm 231D is orthogonal to the fourth axis $O_4$, extends linearly toward the base 22, and supports the fourth joint 232D (the fixed part) at the distal end thereof.

The fifth joint 232E extends substantially parallel to the fourth axis $O_4$, is connected to the basal end of the fourth arm 231D with the movable part (not illustrated) positioned on one end side, and is connected to the fifth arm 231E with the fixed part (not illustrated) positioned on the other end side. In the fifth joint 232E, the movable part is rotatable about a fifth axis $O_5$ relative to the fixed part. Consequently, the fifth joint 232E enables the fourth arm 231D (the imaging unit 21) to rotate about the fifth axis $O_5$.

The fifth axis $O_5$ is an axis parallel to the fourth axis $O_4$.

The fifth arm 231E has a substantially L shape including a first part extending in the vertical direction and a second part extending while being bent at substantially the right angle relative to the first part and supports the fifth joint 232E (fixed part) with the first part.

The sixth joint 232F extends in the vertical direction and is connected to the second part of the fifth arm 231E with the movable part (not illustrated) positioned on one end side, and the fixed part (not illustrated) positioned on the other end side thereof is fixed to a top face of the base 22. In the sixth joint 232F, the movable part is rotatable about a sixth axis $O_6$ relative to the fixed part. Consequently, the sixth joint 232F enables the fifth arm 231E (the imaging unit 21) to rotate about the sixth axis $O_6$.

The sixth axis $O_6$ is an axis along the vertical direction.

In the first embodiment, the inertia of the support unit 23 is set to $2.5 \times 10^{-3}$ $kgm^2$. The inertia of a support unit in a known optical microscope (a microscope in which an magnifying optical system for observing a microscopic site of a part under operation of a patient in a magnified manner is provided at the distal end of the support unit of a support arm apparatus (refer to Japanese Patent Application Laid-open No. 2004-267774, for example)) is about 2.5 $kgm^2$. In other words, the inertia of the support unit 23 is set to about $\frac{1}{1,000}$ of that of the known optical microscope.

The inertia of the support unit 23 is not limited to the value and may be set to any other value so long as it is $1 \times 10^{-2}$ $kgm^2$ or less.

The inertia of the support unit 23 is thus set to be small, whereby the motion of the six degrees of freedom in the support unit 23 (the movement of the imaging unit 21) may be made smooth.

The control apparatus 24 is provided within the base 22 and comprehensively controls the operation of the medical observation system 1. FIG. 1 illustrates the control apparatus 24 outside the base 22 for the convenience of description. As illustrated in FIG. 1, this control apparatus 24 includes a controller 241 and a memory 242.

The controller 241 includes a central processing unit (CPU) and comprehensively controls the operation of the medical observation system 1 in accordance with a control program recorded in the memory 242.

Specifically, the controller 241 switches an operational mode of the support unit 23 in accordance with a user operation by the operator on an operation switching switch (not illustrated) provided in the imaging unit 21 and executes processing responsive to the switched operational mode.

In the first embodiment, the operational mode of the support unit 23 includes a fixed mode, an all-free mode, and an XY movement operational mode.

The fixed mode is an operational mode in which the rotation of the respective movable parts relative to the respective fixed parts of the first to sixth joints 232A to 232F is stopped by brakes, whereby the position and the attitude of the imaging unit 21 are fixed. In other words, the support unit 23 is provided with the brakes (brakes 45 and 55 illustrated in FIG. 5, for example) that stop the rotation of the respective movable parts relative to the respective fixed parts of the first to sixth joints 232A to 232F under control by the controller 241.

The all-free mode is a state in which the rotation of the respective movable parts relative to the respective fixed parts of the first to sixth joints 232A to 232F is allowed by the release of the brakes and is an operational mode that may adjust the position and the attitude of the imaging unit 21 through a direct operation by the operator (an operation by the operator that holds the imaging unit 21 in his/her hand to directly move the imaging unit 21, for example).

The XY movement operational mode is an operational mode that moves the imaging field of view by the imaging unit 21 in any of eight moving directions Ar1 to Ar8 (refer to FIG. 6A) including an X-axial direction and a Y-axial direction in accordance with a user operation by the operator on the foot switch 25. In other words, the support unit 23 is provided with X- and Y-axial actuators 4 and 5 (refer to FIG. 5) that operate the second and third joints 232B and 232C, respectively, under control by the controller 241. A detailed configuration of the X- and Y-axial actuators 4 and 5 will be described below.

The controller 241 executes various kinds of image processing (magnification processing according to an electronic zooming function, for example) on the image signal output from the imaging unit 21 and outputs the image signal after the image processing to the display apparatus 3.

The memory 242 records therein information for the processing by the controller 241 (an X-axial speed profile for controlling an X-axial motor 41 included in the X-axial actuator 4 and a Y-axial speed profile for controlling a Y-axial motor 51 included in the Y-axial actuator 5, for example) apart from the control program that the controller 241 executes. The X-axial speed profile corresponds to a first speed profile according to the present disclosure. The Y-axial speed profile corresponds to a second speed profile according to the present disclosure. The details of the X- and Y-axial speed profiles will be described below.

The foot switch 25 is a part that the operator operates with his/her foot and is used during the XY movement operational mode as described above. Specifically, the foot switch 25 receives an instruction (a user operation) to move the imaging field of view in any of the eight moving directions Ar1 to Ar8 (refer to FIG. 6A) by the operator. The foot switch 25 then outputs an instruction signal responsive to the instruction to move the imaging field of view to the controller 241.

A unit that receives the instruction to move the imaging field of view (an operation receiving unit) is not limited to the foot switch 25; others such as a switch that the operator operates with his/her hand may be employed.

The display apparatus 3 includes a display using liquid crystals, organic electro luminescence (EL), or the like and displays an image based on the image signal output from the imaging unit 21 and subjected to the various kinds of image processing by the controller 241.

Use Example of Medical Observation System

The following describes a use example of the medical observation system 1.

Figure 2:
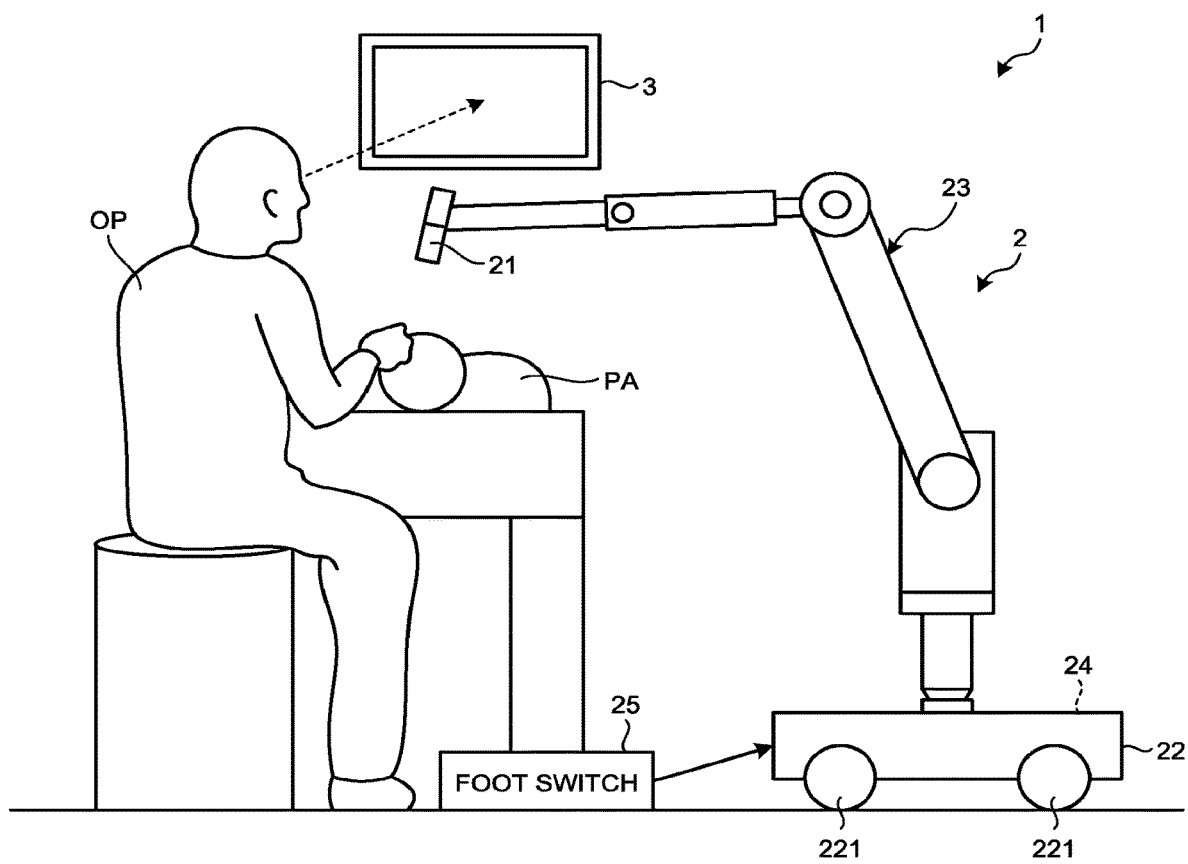
FIG. 2 is a diagram schematically illustrating a situation of an operation using the medical observation system.

FIG. 2 is a diagram schematically illustrating a situation of an operation using the medical observation system 1.

First, an operator OP positions the imaging unit 21 over a target object of a patient PA lying on an operating table (the head of the patient PA in the example of FIG. 2). In the all-free mode, for example, the operator OP holds the imaging unit 21 and positions the imaging unit 21 over the target object using the motion with the six degrees of freedom of the support unit 23. In the XY movement operational mode, the operator OP performs an operation (an instruction to move the imaging field of view in any of the eight moving directions Ar1 to Ar8 (refer to FIG. 6A)) on the foot switch 25, thereby positioning the imaging unit 21 over the target object.

The image taken by the imaging unit 21 is magnified with a predetermined magnification by the optical zooming function of the imaging unit 21 and the electronic zooming function by the controller 241 and is displayed on the display apparatus 3 mounted on a wall of an operating room.

The operator OP then executes an operation while checking the image displayed on the display apparatus 3.

The following describes a problem when the imaging field of view is moved.

Figures 3, 4:
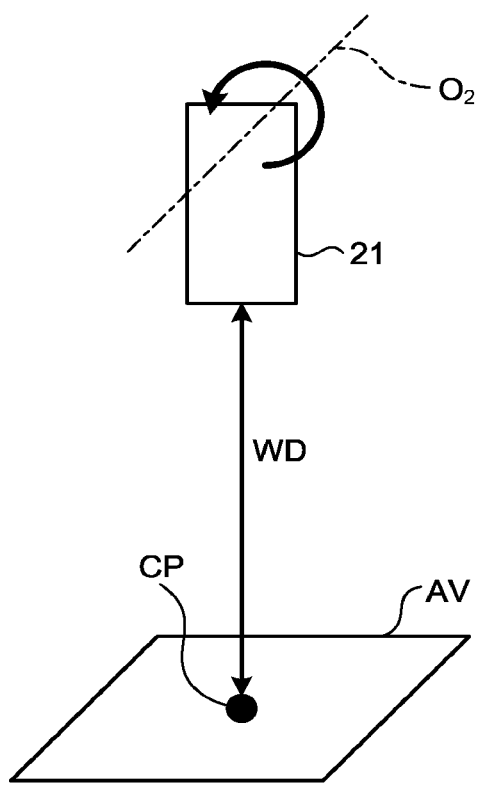
FIG. 3 is a diagram illustrating a problem when an imaging field of view is moved.
FIG. 4 is a diagram illustrating the problem when the imaging field of view is moved.

FIG. 3 and FIG. 4 are diagrams illustrating the problem when an imaging field of view AV is moved. Specifically, FIG. 3 illustrates the positional relation between the imaging field of view (an actual field of view) AV and the imaging unit 21. FIG. 4 illustrates the relation among a working distance WD (the distance from the target object to the imaging unit 21), a magnification (a variable magnification ratio) by the optical zooming function, a magnification by the electronic zooming function (the example of FIG. 4 illustrates only electronic zooming function off), and the size of the imaging field of view AV.

When the working distance WD is 400 mm, the magnification by the optical zooming function is 6× (a variable magnification ratio) (electronic zooming function off), for example, the size of the imaging field of view AV is diagonally 25 mm as illustrated in FIG. 4. An angle change θ about the second axis $O_2$ (or the third axis $O_3$) when the imaging unit 21 is rotated about the second axis $O_2$ (or the third axis $O_3$) until a point CP positioned at the center of the imaging field of view AV is positioned outside the imaging field of view AV (the point CP disappears from the screen of the display apparatus 3 (the image vanishes)) is 1.8 degrees as shown in the following Formula (1).

$$\theta = \tan^{-1}\frac{25}{2\times 400} = 1.8° \qquad (1)$$

When the distance from the distal end of the imaging unit 21 to the second axis $O_2$ is set to 100 mm, 1.8 degrees as an angle change corresponds to a movement of 3 mm of the distal end of the imaging unit 21. In other words, by rotating the imaging unit 21 by 1.8 degrees alone, or in other words, by moving the distal end of the imaging unit 21 by 3 mm alone, the image vanishes. The image vanishing is produced by a smaller angle change θ (a smaller amount of movement of the distal end of the imaging unit 21) as the magnification increases.

The inertia of the support unit 23 is set to the extremely small value ($2.5\times 10^{-3}$ kgm$^2$) as described above, through the application of a weak force to the imaging unit 21 by the operator OP alone, the image vanishes. For this reason, in the first embodiment, the second and third joints 232B and 232C are provided with X- and Y-axial load imparting mechanisms 6 and 7 (refer to FIG. 5), respectively, in order to prevent the image vanishing. A detailed configuration of the X- and Y-axial load imparting mechanisms 6 and 7 will be described below.

Configuration of X- and Y-Axial Actuators

The following describes a configuration of the X- and Y-axial actuators 4 and 5.

Figure 5:
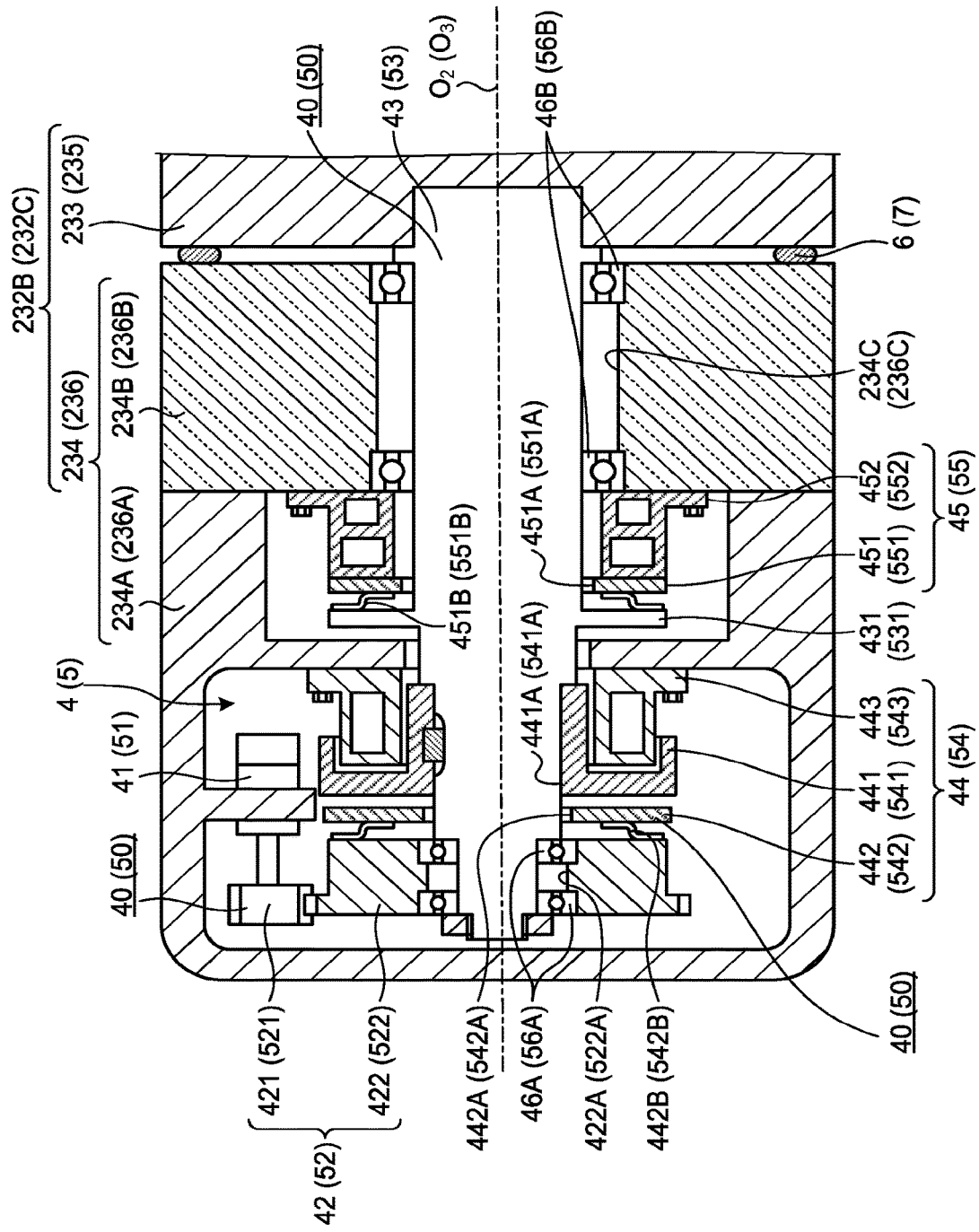
FIG. 5 is a sectional view of a configuration of X- and Y-axial actuators.

FIG. 5 is a sectional view of the configuration of the X- and Y-axial actuators 4 and 5.

The second and third joints 232B and 232C have a similar configuration. The X- and Y-axial actuators 4 and 5 have a similar configuration. For this reason, FIG. 5 adds respective symbols with parentheses indicating the configuration of the third joint 232C and the Y-axial actuator 5 after respective symbols indicating the configuration of the second joint 232B and the X-axial actuator 4.

As illustrated in FIG. 5, the X-axial actuator 4 is provided within the fixed part 234 included in the second joint 232B.

For this reason, before describing the configuration of the X-axial actuator 4, the following describes a configuration of the fixed part 234 with reference to FIG. 5.

The fixed part 234 includes a housing 234A and a blocking part 234B.

The housing 234A has a bottomed cylindrical shape the central axis of which overlaps with the second axis $O_2$ and is fixed to the distal end of the second arm 231B.

The blocking part 234B has an annular shape having a through hole 234C and is fixed to the housing 234A so as to block an opening of the housing 234A.

As illustrated in FIG. 5, the X-axial actuator 4 includes an X-axial motor 41, a speed reduction mechanism 42, a drive shaft 43, a clutch 44, and a brake 45.

The X-axial motor 41 includes a general electric motor controlled by the controller 241 and is a power source that gives power to the second joint 232B. In other words, the X-axial motor 41 corresponds to a first motor according to the present disclosure. The X-axial motor 41 is mounted on an inner face of the housing 234A so as to cause an output shaft of the X-axial motor 41 to be parallel to the second axis $O_2$.

The speed reduction mechanism 42 is provided on the output shaft of the X-axial motor 41 and reduces the speed of the rotation of the output shaft with a predetermined speed reduction rate. This speed reduction mechanism 42 includes a plurality of gears that mesh with each other. In the first embodiment, the gears include a first spur gear 421 fixed to the output shaft of the X-axial motor 41 and a second spur gear 422 that meshes with the first spur gear 421.

The number of the gears included in the speed reduction mechanism 42 is not limited to two and may be three or more. The gears included in the speed reduction mechanism 42 are not limited to the spur gears and may be other gears.

Out of the first and second spur gears 421 and 422, the second spur gear 422 is arranged within the housing 234A so as to cause the central axis thereof to overlap with the second axis $O_2$. The second spur gear 422 is formed with a through hole 422A passing through along the central axis.

The drive shaft 43 has a cylindrical shape and is installed so as to cause the central axis of the cylinder to overlap with the second axis $O_2$. Specifically, one end side of the drive shaft 43 is inserted into the through hole 422A and is pivotally supported rotatably relative to the second spur gear 422 via a first bearing 46A. The other end side of the drive shaft 43 is inserted into the through hole 234C and is pivotally supported rotatably relative to the blocking part 234B via a second bearing 46B with the other end protruding outside the fixed part 234. In other words, the drive shaft 43 is rotatable about the central shaft relative to the fixed part 234. The other end of the drive shaft 43 is fixed to the movable part 233.

As illustrated in FIG. 5, the clutch 44 includes a rotor 441, an armature 442, and a stator 443.

The rotor 441 has a through hole 441A and is fixed to the drive shaft 43 with the drive shaft 43 inserted into the through hole 441A.

The armature 442 has a disc shape and has a through hole 442A passing through along the central axis of the disc. The armature 442 is arranged in between the second spur gear 422 and the rotor 441 with the drive shaft 43 inserted into the through hole 442A. The armature 442 is mounted on the second spur gear 422 via a leaf spring 442B and is movable along the second axis $O_2$ in accordance with the elastic deformation of the leaf spring 442B.

The stator 443 is fixed to the housing 234A and advances and retracts the armature 442 along the second axis $O_2$ under control by the controller 241. With the armature 442 being separate from the rotor 441, the speed reduction mechanism 42 and the drive shaft 43 are in a disengaged state (clutch off), in which they are not connected to each other via the clutch 44. In other words, the drive shaft 43 does not rotate along with the rotation of the X-axial motor 41. In contrast, with the armature 442 being in contact with the rotor 441, the speed reduction mechanism 42 and the drive shaft 43 are in an allowed state (clutch on), in which they are connected to each other via the clutch 44. In other words, the drive shaft 43 rotates along with the rotation of the X-axial motor 41, transmits the rotation of the X-axial motor 41 to the movable part 233, and rotates the movable part 233 about the second axis $O_2$.

As illustrated in FIG. 5, the brake 45 includes an armature 451 and a stator 452.

The armature 451 has a disc shape and has a through hole 451A that passes through along the central axis of the disc and into which the drive shaft 43 is inserted. The armature 451 is mounted on a flange 431 provided on the outer peripheral face of the drive shaft 43 via a leaf spring 451B and is movable along the second axis $O_2$ in accordance with the elastic deformation of the leaf spring 451B.

The stator 452 is fixed to the blocking part 234B and advances and retracts the armature 451 along the second axis $O_2$ under control by the controller 241. With the armature 451 being separate from the stator 452, the stator 452 releases the armature 451 to allow the rotation of the drive shaft 43. In contrast, with the armature 451 being in contact with the stator 452, the stator 452 restrains the rotation of the armature 451 (the drive shaft 43).

The configurations of the third joint 232C and the Y-axial actuator 5 are similar to the configurations of the second joint 232B and the X-axial actuator 4, respectively. In other words, as illustrated in FIG. 5, the fixed part 236 included in the third joint 232C has a housing 236A and a blocking part 236B (a through hole 236C) that are similar to the housing 234A and the blocking part 234B (the through hole 234C), respectively, included in the fixed part 234 of the second joint 232B. The Y-axial actuator 5 includes a Y-axial motor 51, a speed reduction mechanism 52 (including first and second spur gears 521 and 522 (including a through hole 522A)), a drive shaft 53 (including a flange 531), a clutch 54 (including a rotor 541 (including a through hole 541A), an armature 542 (including a through hole 542A and a leaf spring 542B), and a stator 543), a brake 55 (including an armature 551 (including a through hole 551A and a leaf spring 551B) and a stator 552), and first and second bearings 56A and 56B that are similar to the X-axial motor 41, the speed reduction mechanism 42 (including the first and second spur gears 421 and 422 (including the through hole 422A)), the drive shaft 43 (including the flange 431), the clutch 44 (including the rotor 441 (including the through hole 441A), the armature 442 (including the through hole 442A and the leaf spring 442B), and the stator 443), the brake 45 (including the armature 451 (including the through hole 451A and the leaf spring 451B), and the stator 452), and the first and second bearings 46A and 46B, respectively, included in the X-axial actuator 4.

The Y-axial motor 51 corresponds to a second motor according to the present disclosure.

The following describes the relation between the moving direction of the imaging field of view AV and the rotational direction of X- and Y-axial motors 41 and 51.

Figures 6A, 6B:
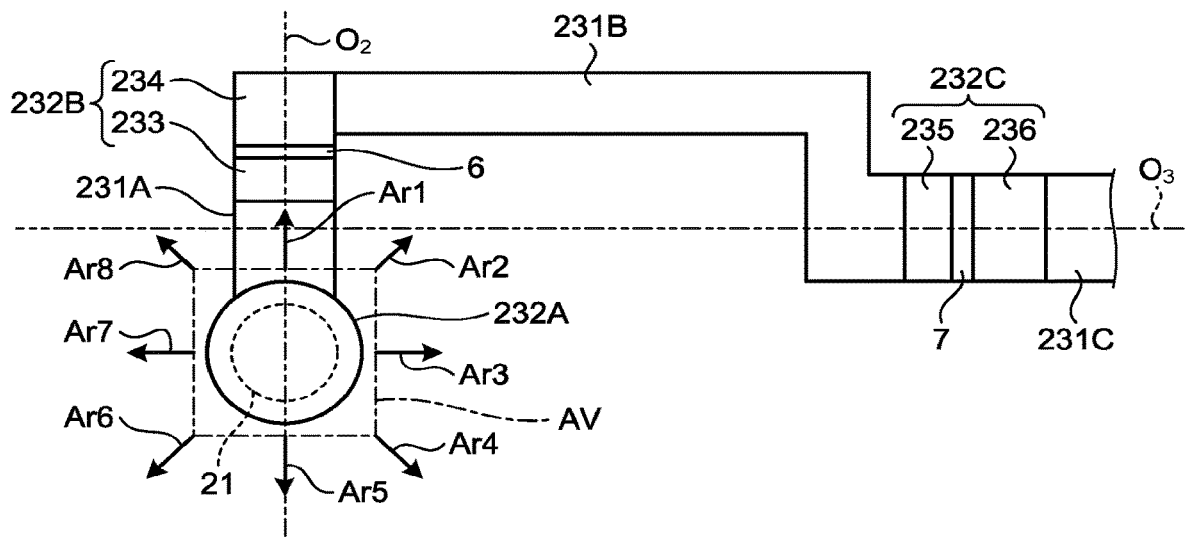
FIG. 6A is a diagram illustrating the relation between the moving direction of the imaging field of view and the rotational direction of X- and Y-axial motors.
FIG. 6B is a diagram illustrating the relation between the moving direction of the imaging field of view and the rotational direction of the X- and Y-axial motors.

FIG. 6A and FIG. 6B are diagrams illustrating the relation between the moving direction of the imaging field of view AV and the rotational direction of the X- and Y-axial motors 41 and 51.

The moving directions Ar1 and Ar5 are directions along the X-axis. For this reason, when the imaging field of view AV is moved in the moving direction Ar1 or the moving direction Ar5, the controller 241 rotates only the Y-axial motor 51 in a forward direction CW or a backward direction CCW opposite to the forward direction CW.

The moving directions Ar3 and Ar7 are directions along the Y-axis. For this reason, when the imaging field of view AV is moved in the moving direction Ar3 or the moving direction Ar7, the controller 241 rotates only the X-axial motor 41 in the forward direction CW or the backward direction CCW.

Further, the moving directions Ar2, Ar4, Ar6, and Ar8 are directions crossing the X-axis and the Y-axis by 45 degrees. In the following section, the moving directions Ar2, Ar4, Ar6, and Ar8 will be denoted as oblique directions Ar2, Ar4, Ar6, and Ar8 for the convenience of description. When the imaging field of view AV is moved in any of the oblique directions Ar2, Ar4, Ar6, and Ar8, the controller 241 rotates both the X- and Y-axial motors 41 and 51 in the forward direction CW or the backward direction CCW.

Configuration of X- and Y-Axial Load Imparting Mechanisms

The following describes the configuration of the X- and Y-axial load imparting mechanisms 6 and 7 with reference to FIG. 5.

The X-axial load imparting mechanism 6 is a mechanism that, when the movable part 233 rotates relative to the fixed part 234, imparts rotational resistance caused by friction to the rotation. In the first embodiment, as illustrated in FIG. 5, the X-axial load imparting mechanism 6 includes an O-ring interposed between the movable part 233 and the fixed part 234 to be compressed by the movable part 233 and the fixed part 234.

The Y-axial load imparting mechanism 7 is a mechanism that, when the movable part 235 rotates relative to the fixed part 236, imparts rotational resistance caused by friction to the rotation. In the first embodiment, as illustrated in FIG. 5, the Y-axial load imparting mechanism 7 includes an O-ring interposed between the movable part 235 and the fixed part 236 to be compressed by the movable part 235 and the fixed part 236 similarly to the X-axial load imparting mechanism 6.

The second joint 232B rotates the entire three components, or the imaging unit 21, the first joint 232A, and the first arm 231A. On the other hand, the third joint 232C rotates the entire five components, or the imaging unit 21, the first joint 232A, the first arm 231A, the second joint 232B, and the second arm 231B. In other words, the third joint 232C is heavier in the weight of an object to be rotated and is larger in inertial force than the second joint 232B.

The separate distance between the second axis $O_2$ and a gripped position (a position that the operator OP holds (the imaging unit 21, for example)) and the separate distance between the third axis $O_3$ and the gripped position are different from each other, and the easiness of rotation about the second axis $O_2$ by the second joint 232B and the easiness of rotation about the third axis $O_3$ by the third joint 232C are different from each other.

Considering the above-described points, the amount of compression of the X-axial load imparting mechanism 6 by the movable part 233 and the fixed part 234 and the amount of compression of the Y-axial load imparting mechanism 7 by the movable part 235 and the fixed part 236 are made different from each other, and the respective frictional forces of the rotational resistance that the X- and Y-axial load imparting mechanisms 6 and 7 impart are made different from each other. In the first embodiment, the Y-axial load imparting mechanism 7 is set to be larger in the amount of compression than the X-axial load imparting mechanism 6 and is set to be stronger in the frictional force of the rotational resistance to be imparted than the X-axial load imparting mechanism 6.

Control Method Executed by Medical Observation Apparatus

The following describes a control method executed by the medical observation apparatus 2.

Figure 7:
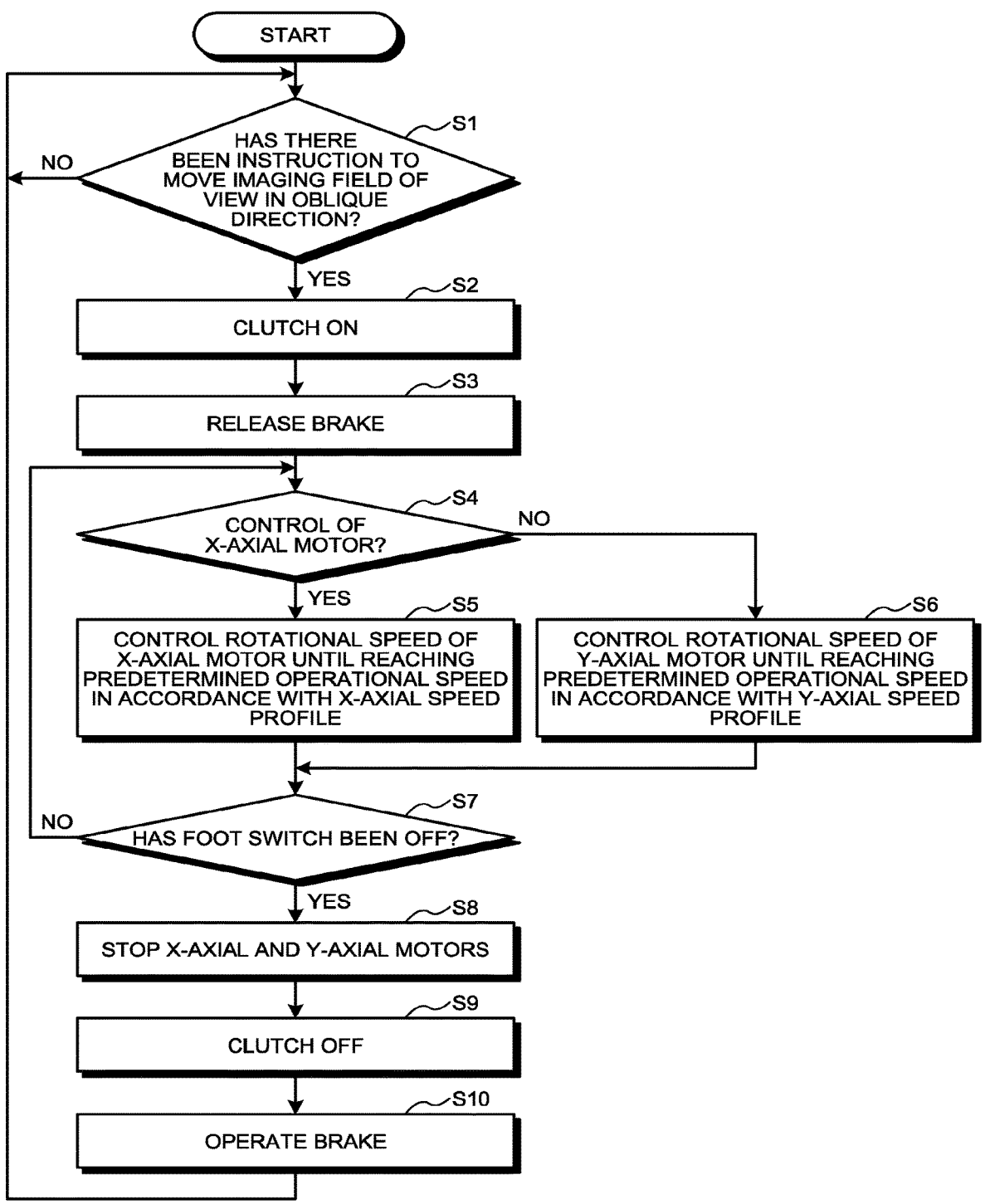
FIG. 7 is a flowchart of a control method executed by the medical observation apparatus.

FIG. 7 is a flowchart of the control method executed by the medical observation apparatus 2.

The following describes a case in which the imaging field of view AV is moved in any of the oblique directions Ar2, Ar4, Ar6, and Ar8 in the XY movement operational mode for the convenience of description. The description starts from a state in which both the clutches 44 and 54 are disengaged (clutch off) and the brakes 45 and 55 are operating (both the drive shafts 43 and 53 are restrained).

First, the controller 241 constantly monitors whether there has been an instruction to move the imaging field of view AV in any of the oblique directions Ar2, Ar4, Ar6, and Ar8 on the foot switch 25 by the operator OP (Step S1).

If it is determined that there has been an instruction to move the imaging field of view AV in any of the oblique directions Ar2, Ar4, Ar6, and Ar8 (Yes at Steo S1), the controller 241 controls each operation of the clutches 44 and 54 to switch each of them from the disengaged state (clutch off) to the allowed state (clutch on) (Step S2).

After Step S2, the controller 241 controls each operation of the brakes 45 and 55 to release each of the brakes 45 and 55 (to allow each rotation of the drive shafts 43 and 53) (Step S3).

After Step S3, the controller 241 reads the X- and Y-axial speed profiles recorded in the memory 242 and controls the operation of both the X- and Y-axial motors 41 and 51 as described below in accordance with the X- and Y-axial speed profiles (Steps S4 to S6: control steps).

Figure 8:
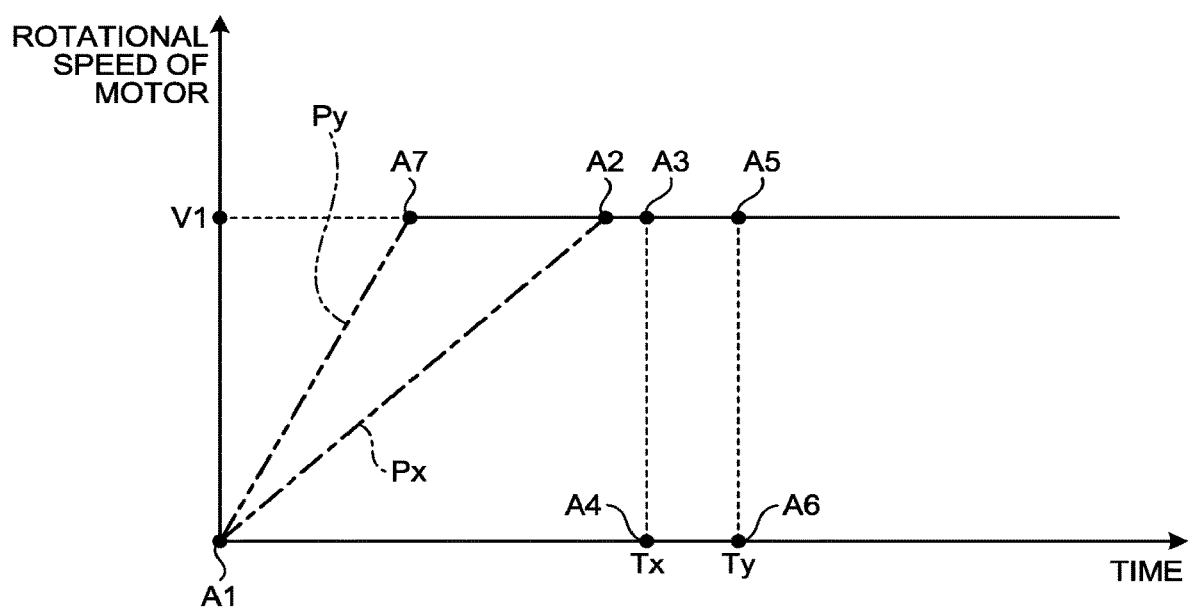
FIG. 8 is a diagram of X- and Y-axial speed profiles recorded in a memory.

FIG. 8 is a diagram of X- and Y-axial speed profiles Px and Py recorded in the memory 242. Specifically, in FIG. 8, the horizontal axis shows time, whereas the vertical axis shows the rotational speed of the X- and Y-axial motors 41 and 51. In FIG. 8, the X-axial speed profile Px is shown by the dashed line, whereas the Y-axial speed profile Py is shown by the chain double-dashed line.

The following assumes a case in which the X-axial motor 41 starts to be driven, and until the rotational speed of the X-axial motor 41 reaches a predetermined operational speed V1, the rotational speed is accelerated at a first acceleration in accordance with the X-axial speed profile Px. In other words, the X-axial speed profile Px is a speed profile that accelerates the rotational speed of the X-axial motor 41 at the first acceleration until the rotational speed reaches the predetermined operational speed V1.

In this case, the movable part 233 does not rotate relative to the fixed part 234 simultaneously when the X-axial motor 41 starts to be driven and starts to rotate after a time Tx (FIG. 8) has elapsed after the X-axial motor 41 has started to be driven. This is ascribable to the fact that an X-axial power transmission mechanism 40 (FIG. 5) that transmits the rotation of the X-axial motor 41 to the movable part 233 gradually becomes elastically deformed in accordance with the rotation of the X-axial motor 41 until balancing with the frictional force of the rotational resistance by the X-axial load imparting mechanism 6. The X-axial power transmission mechanism 40 corresponds to the speed reduction mechanism 42, the drive shaft 43, the clutch 44, and the like. In other words, at a point in time (the time Tx) when the amount of elastic deformation of the X-axial power transmission mechanism 40 has exceeded a predetermined amount responsive to the frictional force, the movable part 233 starts to rotate relative to the fixed part 234.

The area of the trapezoidal area surrounded by A1 to A4 illustrated in FIG. 8 is the amount of rotation of the X-axial motor 41 until the movable part 233 rotates and corresponds to the amount of elastic deformation of the X-axial power transmission mechanism 40.

Assumed is a case in which the Y-axial motor 51 starts to be driven, and until the rotational speed of the Y-axial motor 51 reaches the predetermined operational speed V1, the rotational speed is accelerated at the first acceleration (a case in which the rotational speed is controlled in accordance with the X-axial speed profile Px) similarly to the case of the X-axial motor 41.

In this case, the movable part 235 does not rotate relative to the fixed part 236 simultaneously when the Y-axial motor 51 starts to be driven and starts to rotate after a time Ty (FIG. 8) has elapsed after the Y-axial motor 51 has started to be driven. This time Ty is a time later than the time Tx. This is ascribable to the fact that a Y-axial power transmission mechanism 50 (FIG. 5) that transmits the rotation of the Y-axial motor 51 to the movable part 235 gradually becomes elastically deformed in accordance with the rotation of the Y-axial motor 51 until balancing with the frictional force of the rotational resistance by the Y-axial load imparting mechanism 7 (a frictional force stronger than the frictional force of the rotational resistance by the X-axial load imparting mechanism 6). The Y-axial power transmission mechanism 50 corresponds to the speed reduction mechanism 52, the drive shaft 53, the clutch 54, and the like. In other words, at a point in time (the time Ty) when the amount of elastic deformation of the Y-axial power transmission mechanism 50 has exceeded a predetermined amount responsive to the frictional force, the movable part 235 starts to rotate relative to the fixed part 236.

The area of the trapezoidal area surrounded by A1, A2, A5, and A6 illustrated in FIG. 8 is the amount of rotation of the Y-axial motor 51 until the movable part 235 rotates and corresponds to the amount of elastic deformation of the Y-axial power transmission mechanism 50.

As described above, when the rotational speeds of the X- and Y-axial motors 41 and 51 are controlled in accordance with the same speed profile, the movable part 233, the imparted frictional force of which is weaker, first starts to rotate. After that, the movable part 235, the imparted frictional force of which is stronger, starts to rotate. In other words, a difference in time at which the movable parts 233 and 235 start to rotate occurs. For this reason, when an instruction to move the imaging field of view AV in any of the oblique directions Ar2, Ar4, Ar6, and Ar8 is performed on the foot switch 25, the imaging field of view AV will first move in the Y-axial direction, and the imaging field of view AV will then move in the oblique direction responsive to the instruction to move the imaging field of view AV. Consequently, the operator OP who checks the image displayed on the display apparatus 3 is given an uncomfortable feeling.

In the first embodiment, the X- and Y-axial speed profiles Px and Py are made different from each other in order to reduce the difference in time at which the movable parts 233 and 235 start to rotate.

Specifically, the X- and Y-axial speed profiles Px and Py are derived as described below. The X-axial speed profile Px is the above-described X-axial speed profile Px for the convenience of description.

First, the times Tx and Ty are actually measured. The Y-axial speed profile Py is derived such that the triangular area surrounded by A1, A7, and A2 illustrated in FIG. 8 will have the same area as the rectangular area surrounded by A3 to A6 illustrated in FIG. 8. In other words, the Y-axial speed profile Py is a speed profile that accelerates the rotational speed of the Y-axial motor 51 at a second acceleration higher than the first acceleration until the rotational speed reaches the predetermined operational speed V1.

The area of the trapezoidal area surrounded by A1, A7, A3, and A4 illustrated in FIG. 8 and the area of the trapezoidal area surrounded by A1, A2, A5, and A6 illustrated in FIG. 8 are the same. In other words, when the Y-axial motor 51 is controlled in accordance with the Y-axial speed profile Py, the movable part 235 will start to rotate simultaneously with the start of the rotation of the movable part 233 (the time Tx after the Y-axial motor 51 has started to be driven).

When executing the control of the X-axial motor 41 (Yes at Step S4), the controller 241 controls the rotational speed of the X-axial motor 41 in accordance with the X-axial speed profile Px until the rotational speed reaches the predetermined operational speed V1 (Step S5: a first control step). After the rotational speed of the X-axial motor 41 has been the predetermined operational speed V1, the controller 241 rotates the X-axial motor 41 at the operational speed V1.

When executing the control of the Y-axial motor 51 (No at Step S4), simultaneously with Step S5 (while the Y-axial motor 51 starts to be driven simultaneously with the X-axial motor 41), the controller 241 controls the rotational speed of the Y-axial motor 51 in accordance with the Y-axial speed profile Py until the rotational speed reaches the predetermined operational speed V1 (Step S6: a second control step). After rotational speed of the Y-axial motor 51 has been the predetermined operational speed V1, the controller 241 rotates the Y-axial motor 51 at the operational speed V1.

The controller 241 constantly monitors whether the operation on the foot switch 25 by the operator OP at Step S1 has been released (whether the foot switch 25 has been OFF) (Step S7) and continues the processing at Steps S4 to S6 while the operation continues. In contrast, if it is determined that the foot switch 25 has been off (Yes at Step S7), the controller 241 stops the drive of the X- and Y-axial motors 41 and 51 (Step S8).

After Step S8, the controller 241 controls each operation of the clutches 44 and 54 to switch each of them from the allowed state (clutch on) to the disengaged state (clutch off) (Step S9).

After Step S9, the controller 241 controls each operation of the brakes 45 and 55 and operates each of the brakes 45 and 55 (restrains each of the drive shafts 43 and 53) (Step S10). After that, the controller 241 returns to Step S1.

In the medical observation apparatus 2 according to the first embodiment described above, the X- and Y-axial speed profiles Px and Py are speed profiles different from each other. The Y-axial load imparting mechanism 7 is set to be stronger in the frictional force of the rotational resistance to be imparted than the X-axial load imparting mechanism 6. The X- and Y-axial speed profiles Px and Py are speed profiles different from each other, whereby the amount of rotation of the Y-axial motor 51 after an instruction to move the imaging field of view AV in any of the oblique directions Ar2, Ar4, Ar6, and Ar8 has been performed may be set to be larger than the amount of rotation of the X-axial motor 41. In other words, the time during which the amount of elastic deformation of the Y-axial power transmission mechanism 50 exceeds the predetermined amount responsive to the frictional force of the rotational resistance by the Y-axial load imparting mechanism 7 may be reduced.

For this reason, when the imaging field of view AV is moved in any of the oblique directions Ar2, Ar4, Ar6, and Ar8, the difference in time at which the movable parts 233 and 235 start to rotate may be reduced. Consequently, the medical observation apparatus 2 according to the first embodiment produces an effect of making it possible to lessen an uncomfortable feeling to be given to the operator OP.

In particular, the Y-axial speed profile Py is derived such that the triangular area surrounded by A1, A7, and A2 illustrated in FIG. 8 will have the same area as the rectangular area surrounded by A3 to A6 illustrated in FIG. 8.

For this reason, when the imaging field of view AV is moved in any of the oblique directions Ar, Ar4, Ar6, and Ar8, the movable parts 233 and 235 may be simultaneously rotated. Consequently, the uncomfortable feeling to be given to the operator OP may be eliminated.

In the medical observation apparatus 2 according to the first embodiment, the X-axial speed profile Px is a speed profile that accelerates the rotational speed of the X-axial motor 41 at the first acceleration until the rotational speed reaches the predetermined operational speed V1. The Y-axial speed profile Py is a speed profile that accelerates the rotational speed of the Y-axial motor 51 at the second acceleration higher than the first acceleration until the rotational speed reaches the predetermined operational speed V1.

For this reason, with the X- and Y-axial speed profiles Px and Py being simple speed profiles, the control of the X- and Y-axial motors 41 and 51 may be easily executed, and a processing load on the controller 241 may be reduced.

Second Embodiment

The following describes a second embodiment of the present disclosure.

In the following description, components similar to those of the first embodiment will be denoted by the same symbols, and detailed descriptions thereof will be omitted or simplified.

The second embodiment is different from the first embodiment only in the X- and Y-axial speed profiles recorded in the memory 242.

The following describes the X- and Y-axial speed profiles according to the second embodiment.

Figure 9:
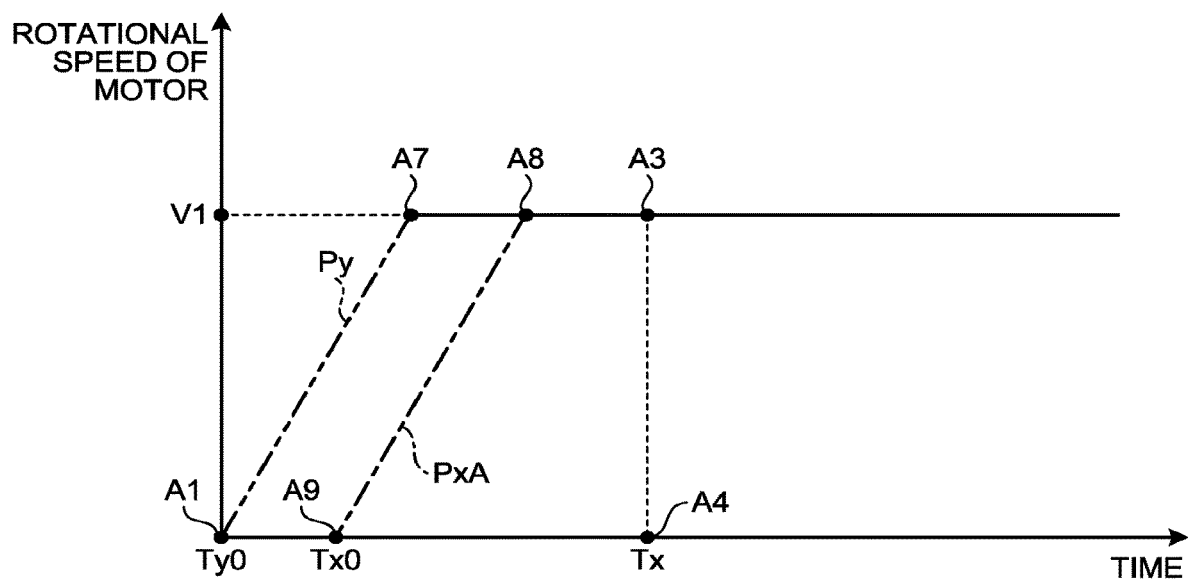
FIG. 9 is a diagram of X- and Y-axial speed profiles according to a second embodiment.

FIG. 9 is a diagram of X- and Y-axial speed profiles PxA and Py according to the second embodiment. Specifically, FIG. 9 is a diagram corresponding to FIG. 8; the X-axial speed profile PxA is shown by the dashed line, whereas the Y-axial speed profile Py is shown by the chain double-dashed line.

As illustrated in FIG. 9, the X- and Y-axial speed profiles PxA and Py according to the second embodiment are made different from each other similarly to the first embodiment.

Specifically, the X-axial speed profile PxA according to the second embodiment is a speed profile that starts the drive of the X-axial motor 41 at a timing Tx0 (FIG. 9) later than a timing Ty0 (FIG. 9) at which the Y-axial motor 51 starts to be driven in the Y-axial speed profile Py. The X- and Y-axial speed profiles PxA and Py according to the second embodiment are speed profiles that, after each of the X- and Y-axial motors 41 and 51 has started to be driven until each of the rotational speeds of the X- and Y-axial motors 41 and 51 reaches the predetermined operational speed V1, accelerate each of the rotational speeds at the same acceleration.

The X- and Y-axial speed profiles PxA and Py according to the second embodiment are derived as described below. The Y-axial speed profile Py is the same speed profile as the Y-axial speed profile Py of the first embodiment for the convenience of description.

First, acceleration for accelerating the rotational speed of the X-axial motor 41 until reaching the predetermined operational speed V1 is the second acceleration of the Y-axial speed profile Py described in the first embodiment. The X-axial speed profile PxA is derived such that the parallelogrammatic area surrounded by A1, A7, A8, and A9 illustrated in FIG. 9 will have the same area as the rectangular area surrounded by A3 to A6 illustrated in FIG. 8.

The area of the trapezoidal area surrounded by A9, A8, A3, and A4 illustrated in FIG. 9 and the area of the trapezoidal area surrounded by A1 to A4 illustrated in FIG. 8 are the same. In other words, when the X-axial motor 41 is controlled in accordance with the X-axial speed profile PxA, the movable part 233 will start to rotate simultaneously with the start of the rotation of the movable part 235 (the time Tx after the Y-axial motor 51 has started to be driven).

A control method according to the second embodiment is different from the control method (FIG. 7) described in the first embodiment only in that at Steps S4 to S6, until the rotational speeds of the X- and Y-axial motors 41 and 51 reach the predetermined operational speed V1, the rotational speeds are controlled in accordance with the X- and Y-axial speed profiles PxA and Py illustrated in FIG. 9.

The second embodiment described above produces the following effect apart from an effect similar to that of the first embodiment.

The X-axial speed profile PxA according to the second embodiment is a speed profile that starts the drive of the X-axial motor 41 at the timing Tx0 later than the timing Ty0 at which the Y-axial motor 51 starts to be driven in the Y-axial speed profile Py. The X- and Y-axial speed profiles PxA and Py according to the second embodiment are speed profiles that, after each of the X- and Y-axial motors 41 and 51 has started to be driven until each of the rotational speeds of the X- and Y-axial motors 41 and 51 reaches the predetermined operational speed V1, accelerate each of the rotational speeds at the same acceleration.

In other words, the X- and Y-axial motors 41 and 51 have only to be rotated at the same acceleration, whereby the control of the X- and Y-axial motors 41 and 51 may be easily performed, and the processing load on the controller 241 may be further reduced.

Third Embodiment

The following describes a third embodiment of the present disclosure.

In the following description, components similar to those of the first embodiment will be denoted by the same symbols, and detailed descriptions thereof will be omitted or simplified.

The third embodiment is different from the first embodiment only in the X- and Y-axial speed profiles recorded in the memory 242.

The following describes the X- and Y-axial speed profiles according to the third embodiment.

Figure 10:
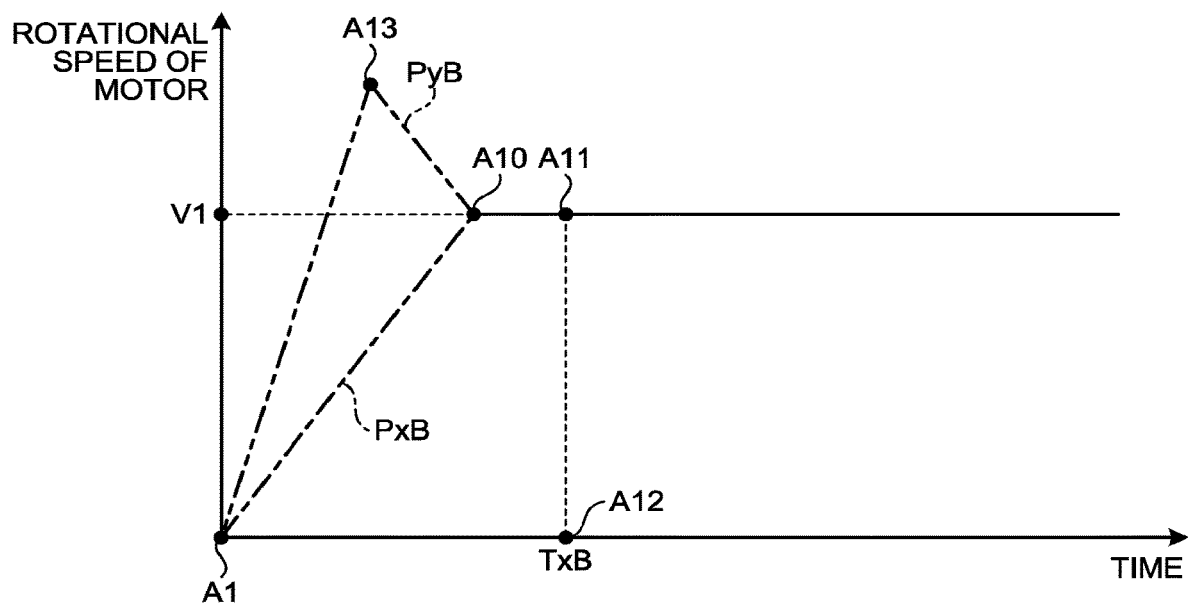
FIG. 10 is a diagram of X- and Y-axial speed profiles according to a third embodiment.

FIG. 10 is a diagram of X- and Y-axial speed profiles PxB and PyB according to the third embodiment. Specifically, FIG. 10 is a diagram corresponding to FIG. 8; the X-axial speed profile PxB is shown by the dashed line, whereas the Y-axial speed profile PyB is shown by the chain double-dashed line.

As illustrated in FIG. 10, the X- and Y-axial speed profiles PxB and PyB according to the third embodiment are made different from each other similarly to the first embodiment.

Specifically, the X-axial speed profile PxB according to the third embodiment is a speed profile that, after the X-axial motor 41 has started to be driven until the rotational speed of the X-axial motor 41 reaches the predetermined operational speed V1, accelerates the rotational speed at a third acceleration. The Y-axial speed profile PyB according to the third embodiment is a speed profile having an acceleration section during which, after the Y-axial motor 51 has started to be driven until the rotational speed of the Y-axial motor 51 reaches the predetermined operational speed V1, the rotational speed is accelerated at a fourth acceleration higher than the third acceleration and is made higher than the operational speed V1 and a deceleration section during which the rotational speed is decelerated to the operational speed V1.

The X- and Y-axial speed profiles PxB and PyB according to the third embodiment are derived as described below:

First, the X-axial speed profile PxB is a speed profile in which acceleration for accelerating the rotational speed of the X-axial motor 41 until reaching the predetermined operational speed V1 is the third acceleration higher than the first acceleration in the X-axial speed profile Px described in the first embodiment.

The area of the trapezoidal area surrounded by A1 and A10 to A12 illustrated in FIG. 10 and the area of the trapezoidal area surrounded by A1 to A4 illustrated in FIG. 8 are the same. In other words, when the X-axial motor 41 is controlled in accordance with the X-axial speed profile PxB, the movable part 233 will start to rotate after a time TxB, which is shorter than the time Tx described in the first embodiment, has elapsed after the X-axial motor 41 has started to be driven.

Acceleration for accelerating the rotation of the Y-axial motor 51 after the Y-axial motor 51 has started to be driven is the fourth acceleration higher than the third acceleration. The Y-axial speed profile PyB is derived such that the triangular area surrounded by A1, A13, and A10 illustrated in FIG. 10 will have the same area as the rectangular area surrounded by A3 to A6 illustrated in FIG. 8.

The area of the area surrounded by A1, A13, and A10 to A12 illustrated in FIG. 10 and the area of the trapezoidal area surrounded by A1, A2, A5, and A6 (the area of the trapezoidal area surrounded by A1, A7, A3, and A4) illustrated in FIG. 8 are the same. In other words, when the Y-axial motor 51 is controlled in accordance with the Y-axial speed profile PyB, the movable part 235 will start to rotate simultaneously with the start of the rotation of the movable part 233 (the time TxB after the Y-axial motor 51 has started to be driven).

A control method according to the third embodiment is different from the control method (FIG. 7) described in the first embodiment only in that at Steps S4 to S6, until the rotational speeds of the X- and Y-axial motors 41 and 51 reach the predetermined operational speed V1, the rotational speeds are controlled in accordance with the X- and Y-axial speed profiles PxB and PyB illustrated in FIG. 10.

The third embodiment described above produces the following effect apart from an effect similar to that of the first embodiment.

The X-axial speed profile PxB according to the third embodiment is a speed profile in which the acceleration for accelerating the rotational speed of the X-axial motor 41 until reaching the predetermined operational speed V1 is the third acceleration higher than the first acceleration in the X-axial speed profile Px described in the first embodiment. The Y-axial speed profile PyB according to the third embodiment is a speed profile having the acceleration section during which, until the rotational speed of the Y-axial motor 51 reaches the predetermined operational speed V1, the rotational speed is accelerated at the fourth acceleration higher than the third acceleration and is made higher than the operational speed V1 and the deceleration section during which the rotational speed is decelerated to the operational speed V1.

For this reason, a start-to-move time TxB at which the movable parts 233 and 235 simultaneously start to move may be shorter than a start-to-move time Tx in the first embodiment.

Fourth Embodiment

The following describes a fourth embodiment of the present disclosure.

In the following description, components similar to those of the first embodiment will be denoted by the same symbols, and detailed descriptions thereof will be omitted or simplified.

The fourth embodiment is different from the first embodiment in the X- and Y-axial speed profiles recorded in the memory 242. The Y-axial motor 51 according to the fourth embodiment includes a stepping motor. The other configuration is similar to that of the first embodiment.

The following describes the X- and Y-axial speed profiles according to the fourth embodiment.

Figure 11:
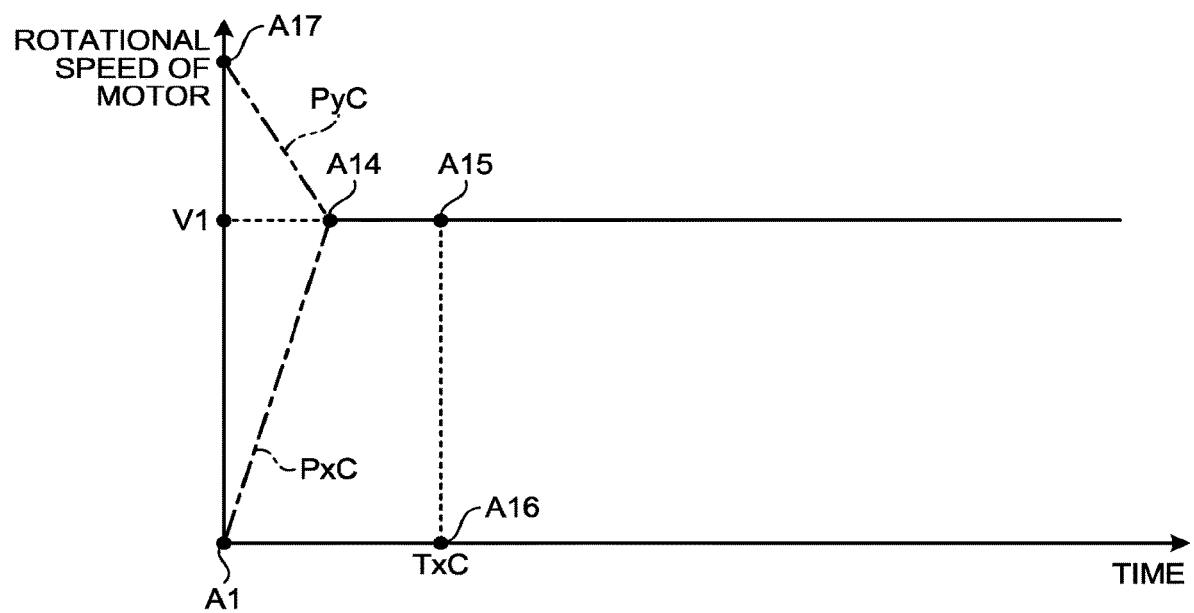
FIG. 11 is a diagram of X- and Y-axial speed profiles according to a fourth embodiment.

FIG. 11 is a diagram of X- and Y-axial speed profiles PxC and PyC according to the fourth embodiment. Specifically, FIG. 11 is a diagram corresponding to FIG. 8; the X-axial speed profile PxC is shown by the dashed line, whereas the Y-axial speed profile PyC is shown by the chain double-dashed line.

As illustrated in FIG. 11, the X- and Y-axial speed profiles PxC and PyC according to the fourth embodiment are made different from each other similarly to the first embodiment.

Specifically, the X-axial speed profile PxC according to the fourth embodiment is a speed profile that, after the X-axial motor 41 has started to be driven until the rotational speed of the X-axial motor 41 reaches the predetermined operational speed V1, accelerates the rotational speed at a fifth acceleration. The Y-axial speed profile PyC according to the fourth embodiment is a speed profile in which an initial speed when the Y-axial motor 51 starts to be driven is made higher than the predetermined operational speed V1.

The X- and Y-axial speed profiles PxC and PyC according to the fourth embodiment are derived as described below.

First, the X-axial speed profile PxC is a speed profile in which acceleration for accelerating the rotational speed of the X-axial motor 41 until reaching the predetermined operational speed V1 is the fifth acceleration higher than the third acceleration in the X-axial speed profile PxB described in the third embodiment.

The area of the trapezoidal area surrounded by A1 and A14 to A16 illustrated in FIG. 11 and the area of the trapezoidal area surrounded by A1 and A10 to A12 illustrated in FIG. 10 are the same. In other words, when the X-axial motor 41 is controlled in accordance with the X-axial speed profile PxC, the movable part 233 will start to rotate after a time TxC, which is shorter than the time TxB described in the third embodiment, has elapsed after the X-axial motor 41 has started to be driven.

The initial speed when the Y-axial motor 51 starts to be driven is made higher than the predetermined operational speed V1. The Y-axial speed profile PyC is derived such that the triangular area surrounded by A1, A17, and A14 illustrated in FIG. 11 will have the same area as the rectangular area surrounded by A3 to A6 illustrated in FIG. 8.

The area of the area surrounded by A1, A17, and A14 to A16 illustrated in FIG. 11 and the area of the trapezoidal area surrounded by A1, A2, A5, and A6 (the area of the trapezoidal area surrounded by A1, A7, A3, and A4) illustrated in FIG. 8 are the same. In other words, when the Y-axial motor 51 is controlled in accordance with the Y-axial speed profile PyC, the movable part 235 will start to rotate simultaneously with the start of the rotation of the movable part 233 (TxC after the Y-axial motor 51 has started to be driven).

A control method according to the fourth embodiment is different from the control method (FIG. 7) described in the first embodiment only in that at Steps S4 to S6, until the rotational speeds of the X- and Y-axial motors 41 and 51 reach the predetermined operational speed V1, the rotational speeds are controlled in accordance with the X- and Y-axial speed profiles PxC and PyC illustrated in FIG. 11.

The fourth embodiment described above produces the following effect apart from an effect similar to that of the first embodiment.

The X-axial speed profile PxC according to the fourth embodiment is a speed profile in which the acceleration for accelerating the rotational speed of the X-axial motor 41 until reaching the predetermined operational speed V1 is the fifth acceleration higher than the third acceleration in the X-axial speed profile PxB described in the third embodiment. The Y-axial speed profile PyC according to the fourth embodiment is a speed profile in which the initial speed when the Y-axial motor 51 starts to be driven is made higher than the predetermined operational speed V1.

For this reason, a start-to-move time TxC at which the movable parts 233 and 235 simultaneously start to move may be shorter than the start-to-move time TxB in the third embodiment.

OTHER EMBODIMENTS

The embodiments for performing the present disclosure have been described; the present disclosure should not be limited by the first to fourth embodiments alone.

Although the X- and Y-axial load imparting mechanisms 6 and 7 are provided in the support unit 23 in the first to fourth embodiments, this is not limiting; the present disclosure also includes a configuration omitting the X- and Y-axial load imparting mechanisms 6 and 7.

In the first to fourth embodiment, the arrangement positions of the second and third joints 232B and 232C and the X- and Y-axial actuators 4 and 5 are not limited to the arrangement positions described in the first to fourth embodiment; they may be arranged at other positions. The arrangement positions of the second and third joints 232B and 232C may be reversed (the X-axial direction and the Y-axial direction illustrated in FIG. 1 may be reversed), for example.

Although the first and second rotation axes according to the present disclosure (the X- and Y-axes) are orthogonal to each other in the first to fourth embodiment, this is not limiting; the present disclosure also includes a configuration in which the first and second rotation axes are not orthogonal to each other.

Although the X- and Y-axial load imparting mechanisms 6 and 7 include the respective O-rings in the first to fourth embodiments, this is not limiting; other configurations may be employed so long as rotational resistance caused by friction is imparted to between the movable part 233 (235) and the fixed part 234 (236).

Although the movable part and the fixed part included in the first to fifth arms 231A to 231E and the first to sixth joints 232A to 232F are separated in the first to fourth embodiments, this is not limiting; at least either the movable part or the fixed part may be formed by the arm, for example.

In the first to fourth embodiments, the X- and Y-axial speed profiles according to the present disclosure are not limited to the X-axial speed profiles Px and PxA to PxC and the Y-axial speed profiles Py, PyB, and PyC described in the first to fourth embodiments and may be other speed profiles. The Y-axial speed profile according to the present disclosure may be any speed profile so long as the area surrounded by the Y-axial speed profile and the X-axial speed profiles Px and PxA to PxC illustrated in FIG. 8 to FIG. 11 is the same as the area of the rectangular area surrounded by A3 to A6 illustrated in FIG. 8, for example.

Figure 12:
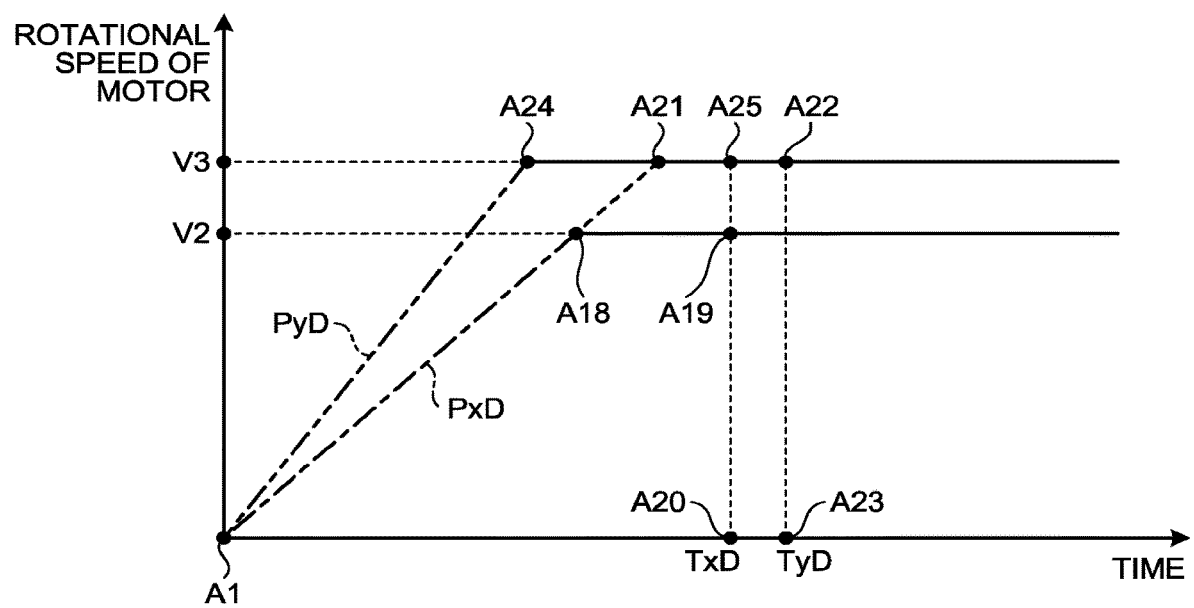
FIG. 12 is a diagram of a modification of the first to fourth embodiments.

FIG. 12 is a diagram of a modification of the first to fourth embodiments. Specifically, FIG. 12 is a diagram corresponding to FIG. 8 to FIG. 11; an X-axial speed profile PxD is shown by the dashed line, whereas a Y-axial speed profile PyD is shown by the chain double-dashed line.

Although the operational speeds of the X- and Y-axial motors 41 and 51 are the same operational speed V1 in the first to fourth embodiments, this is not limiting; as illustrated in FIG. 12, the operational speed of the X-axial motor 41 may be an operational speed V2, whereas the operational speed of the Y-axial motor 51 may be an operational speed V3. In other words, the imaging field of view AV may be movable in an oblique direction crossing the X- and Y-axes at an angle other than 45 degrees.

Assumed is a case in which the X-axial motor 41 starts to be driven, and until the rotational speed of the X-axial motor 41 reaches the predetermined operational speed V2, the rotational speed is accelerated at a sixth acceleration in accordance with the X-axial speed profile PxD.

In this case, the movable part 233 starts to rotate after a time TxD (FIG. 12) has elapsed after the X-axial motor 41 has started to be driven owing to the frictional force of the rotational resistance by the X-axial load imparting mechanism 6 and the elastic deformation of the X-axial power transmission mechanism 40.

The area of the trapezoidal area surrounded by A1, A18, A19, and A20 illustrated in FIG. 12 is the amount of rotation of the X-axial motor 41 until the movable part 233 rotates and corresponds to the amount of elastic deformation of the X-axial power transmission mechanism 40.

Assumed is a case in which the Y-axial motor 51 starts to be driven, and until the rotational speed of the Y-axial motor 51 reaches the predetermined operational speed V3, the rotational speed is accelerated at the sixth acceleration (the dashed line and the broken line in FIG. 12) similarly to the case of the X-axial motor 41.

In this case, the movable part 235 starts to rotate after a time TyD (FIG. 12), which is later than the time TxD, has elapsed after the Y-axial motor 51 has started to be driven owing to the frictional force of the rotational resistance by the Y-axial load imparting mechanism 7 (the frictional force stronger than the frictional force of the rotational resistance by the X-axial load imparting mechanism 6) and the elastic deformation of the Y-axial power transmission mechanism 50.

The area of the trapezoidal area surrounded by A1 and A21 to A23 illustrated in FIG. 12 is the amount of rotation of the Y-axial motor 51 until the movable part 235 rotates and corresponds to the amount of elastic deformation of the Y-axial power transmission mechanism 50.

As described above, when the rotational speeds of the X- and Y-axial motors 41 and 51 are controlled in accordance with the same speed profile, a difference in time at which the movable parts 233 and 235 start to rotate occurs similarly to the first to fourth embodiments. For this reason, when an instruction to move the imaging field of view AV in the oblique direction crossing the X- and Y-axes at an angle other than 45 degrees has been performed on the foot switch 25, the imaging field of view AV will first move in the Y-axial direction, and the imaging field of view AV will then move in the oblique direction responsive to the instruction to move the imaging field of view AV.

Consequently, also in the modification, the X- and Y-axial speed profiles PxD and PyD are preferably made different from each other.

Specifically, the X- and Y-axial speed profiles PxD and PyD are derived as described below. The X-axial speed profile PxD is the above-described X-axial speed profile PxD for the convenience of description.

First, the times TxD and TyD are actually measured. The Y-axial speed profile PyD is derived such that the triangular area surrounded by A1, A24, and A21 illustrated in FIG. 12 will have the same area as the rectangular area surrounded by A20, A25, A22, and A23 illustrated in FIG. 12.

The area of the trapezoidal area surrounded by A1, A24, A25, and A20 illustrated in FIG. 12 and the area of the trapezoidal area surrounded by A1 and A21 to A23 illustrated in FIG. 12 are the same. In other words, when the Y-axial motor 51 is controlled in accordance with the Y-axial speed profile PyD, the movable part 235 will start to rotate simultaneously with the start of the rotation of the movable part 233 (the time TxD after the Y-axial motor 51 has started to be driven).

The medical observation apparatus, the medical observation system, and the control method according to the present disclosure produce an effect of making it possible to lessen an uncomfortable feeling to be given to an operator.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical observation apparatus comprising:
  an imaging sensor configured to image a target object in a magnified manner;
  a support configured to support the imaging sensor, the support including
    a plurality of arms,
    a first joint that connects two of the arms with each other and relatively rotates the two arms about a first rotation axis in accordance with given power,
    a second joint that connects two of the arms with each other and relatively rotates the two arms about a second rotation axis in accordance with given power,
    a first motor that gives the power to the first joint, and
    a second motor that gives the power to the second joint; and
  circuitry configured to control a rotational speed of the first motor in accordance with a first speed profile until the rotational speed reaches a first predetermined operational speed, and control a rotational speed of the second motor in accordance with a second speed profile that is different from the first speed profile until the rotational speed reaches a second predetermined operational speed.

2. The medical observation apparatus according to claim 1, wherein an observation optical axis of the imaging sensor, the first rotation axis, and the second rotation axis are orthogonal to each other.

3. The medical observation apparatus according to claim 1, further comprising:
a first friction material that, when the two arms connected with the first joint relatively rotate, imparts rotational resistance caused by friction to the rotation; and
a second friction material that, when the two arms connected with the second joint relatively rotate, imparts rotational resistance whose frictional force is different from the rotational resistance that the first friction material imparts to the rotation.

4. The medical observation apparatus according to claim 3, wherein
the frictional force of the rotational resistance that the second friction material imparts is set to be stronger than a frictional force of the rotational resistance that the first friction material imparts,
the first speed profile is a speed profile having a section during which the rotational speed of the first motor is accelerated at a first acceleration, and
the second speed profile is a speed profile having a section during which the rotational speed of the second motor is accelerated at a second acceleration higher than the first acceleration.

5. The medical observation apparatus according to claim 3, wherein
the frictional force of the rotational resistance that the second friction material imparts is set to be stronger than the frictional force of the rotational resistance that the first friction material imparts, and
the first speed profile is a speed profile that starts drive of the first motor at a timing later than a timing at which the second motor starts to be driven in the second speed profile.

6. The medical observation apparatus according to claim 3, wherein
the frictional force of the rotational resistance that the second friction material imparts is set to be stronger than a frictional force of the rotational resistance that the first friction material imparts, and
the second speed profile is a speed profile having a section during which the rotational speed of the second motor is a rotational speed higher than the second predetermined operational speed.

7. The medical observation apparatus according to claim 3, wherein
the frictional force of the rotational resistance that the second friction material imparts is set to be stronger than a frictional force of the rotational resistance that the first friction material imparts,
the first speed profile is a speed profile having a section during which the rotational speed of the first motor is accelerated at a third acceleration, and
the second speed profile is a speed profile having an acceleration section during which the rotational speed of the second motor is accelerated at a fourth acceleration that is higher than the third acceleration and a deceleration section during which the rotational speed is decelerated.

8. The medical observation apparatus according to claim 3, wherein
the frictional force of the rotational resistance that the second friction material imparts is set to be stronger than a frictional force of the rotational resistance that the first friction material imparts, and
the second speed profile is a speed profile in which an initial speed when the second motor starts to be driven is made higher than the second predetermined operational speed.

9. The medical observation apparatus according to claim 1, wherein the circuitry is further configured to simultaneously start relative rotation of the two arms connected with the first joint and relative rotation of the two arms connected with the second joint.

10. A medical observation system comprising:
the medical observation apparatus according to claim 1; and
a display apparatus that displays an image taken by the imaging sensor.

11. A control method executed by the medical observation apparatus according to claim 1, the method comprising:
controlling the rotational speed of the first motor in accordance with the first speed profile until the rotational speed reaches the first predetermined operational speed; and
controlling the rotational speed of the second motor in accordance with the second speed profile that is different from the first speed profile until the rotational speed reaches the second predetermined operational speed.

12. The control method executed by the medical observation apparatus according to claim 11, the control method further comprising
simultaneously starting relative rotation of the two arms connected with the first joint and relative rotation of the two arms connected with the second joint.

13. The medical observation apparatus according to claim 1, wherein the first speed profile is a speed profile having a section during which the rotational speed of the first motor is accelerated at a first acceleration, and
the second speed profile is a speed profile having a section during which the rotational speed of the second motor is accelerated at the second acceleration higher than the first acceleration.

14. The medical observation apparatus according to claim 1, wherein the first speed profile is a speed profile that starts drive of the first motor at a timing later than a timing at which the second motor starts to be driven in the second speed profile.

15. The medical observation apparatus according to claim 1, wherein the second speed profile is a speed profile having a section during which the rotational speed of the second motor is a rotational speed higher than the second predetermined operational speed.

16. The medical observation apparatus according to claim 1, wherein the first speed profile is a speed profile having a section during which the rotational speed of the first motor is accelerated at a third acceleration, and
the second speed profile is a speed profile having an acceleration section during which the rotational speed of the second motor is accelerated at a fourth acceleration that is higher than the third acceleration and a deceleration section during which the rotational speed is decelerated.

17. The medical observation apparatus according to claim 1, wherein the second speed profile is a speed profile in which an initial speed when the second motor starts to be driven is made higher than the second predetermined operational speed.

* * * * *